United States Patent
Kostner et al.

(10) Patent No.: US 10,254,142 B2
(45) Date of Patent: Apr. 9, 2019

(54) FLOW SENSOR FOR DETERMINING AN AIR BUBBLE, PARTICULARLY IN A CATHETER, AND CORRESPONDING METHOD

(71) Applicant: Sensirion AG, Staefa ZH (CH)

(72) Inventors: Stefan Kostner, Staefa ZH (CH); Lukas Mahler, Staefa ZH (CH); Niculin Saratz, Staefa ZH (CH)

(73) Assignee: SENSIRION AG, Staefa ZH (CH)

( * ) Notice: Subject to any disclaimer, the term of this patent is extended or adjusted under 35 U.S.C. 154(b) by 148 days.

(21) Appl. No.: 15/346,757

(22) Filed: Nov. 9, 2016

(65) Prior Publication Data
US 2017/0138774 A1 May 18, 2017

(30) Foreign Application Priority Data

Nov. 13, 2015 (EP) .................................... 15194582

(51) Int. Cl.
| | |
|---|---|
| *G01F 1/68* | (2006.01) |
| *A61M 1/16* | (2006.01) |
| *G01F 1/688* | (2006.01) |
| *A61M 5/168* | (2006.01) |
| *G01F 1/74* | (2006.01) |
| *A61M 5/36* | (2006.01) |

(52) U.S. Cl.
CPC ........... *G01F 1/6888* (2013.01); *A61M 5/168* (2013.01); *A61M 5/365* (2013.01); *G01F 1/68* (2013.01); *G01F 1/74* (2013.01); *A61M 2205/3334* (2013.01); *A61M 2205/3368* (2013.01); *A61M 2205/3653* (2013.01)

(58) Field of Classification Search
CPC ................ A61M 5/365; A61M 1/3626; A61M 5/16831; A61M 5/36; G01F 1/6888; G01F 1/6847; G01F 1/6884; G01N 2291/02433; G01N 2015/0011
See application file for complete search history.

(56) References Cited

U.S. PATENT DOCUMENTS

| | | | | |
|---|---|---|---|---|
| 5,533,412 A | * | 7/1996 | Jerman | .................. G01F 1/6842 73/204.26 |
| 2001/0029781 A1 | | 10/2001 | Tai et al. | |
| 2003/0115952 A1 | | 6/2003 | Mayer et al. | |
| 2007/0113644 A1 | * | 5/2007 | Manaka | .................. G01F 1/684 73/204.26 |
| 2008/0210002 A1 | | 9/2008 | Kamiunten et al. | |
| 2009/0078047 A1 | * | 3/2009 | Dam | .................... A61M 1/3626 73/606 |
| 2011/0308328 A1 | * | 12/2011 | Haartsen | ................ A61M 5/365 73/861.41 |
| 2012/0291540 A1 | * | 11/2012 | Cooke | ................ A61M 5/16831 73/204.11 |
| 2017/0184433 A1 | * | 6/2017 | Kostner | ................. G01F 1/6888 |

FOREIGN PATENT DOCUMENTS

WO      WO 9502164      1/1995

* cited by examiner

*Primary Examiner* — Harshad R Patel
(74) *Attorney, Agent, or Firm* — JMB Davis Ben-David

(57) ABSTRACT

The invention relates to a flow sensor (1) and a method for determining the presence of a gas bubble (G) in a liquid (L) flowing through the flow sensor (1).

15 Claims, 3 Drawing Sheets

FLOW SENSOR FOR DETERMINING AN AIR BUBBLE, PARTICULARLY IN A CATHETER, AND CORRESPONDING METHOD

CROSS-REFERENCE TO RELATED APPLICATIONS

Benefit is claimed to European Patent Application No. 15194582, filed Nov. 13, 2015; the content of which are incorporated by reference herein in its entirety.

FIELD

The invention relates to a flow sensor, particularly for measuring the flow velocity, mass flow rate, and/or volumetric flow rate of a fluid medium (e.g. a gas, liquid or mixture of a gas and a liquid), particularly of a medical infusion liquid.

BACKGROUND

It is known in the state-of-the-art to measure the flow velocity or the mass or volumetric flow rate of a liquid and/or gaseous medium by means of a flow sensor on which a heat source and a suitable temperature sensing means are arranged. The flow leads to a change in the temperature distribution generated by the thermal source which can be measured using the temperature sensing means.

The detection of gas (air) bubbles in a liquid flow is of interest e.g. in a medical infusion because air supplied to a patient's blood vessels can be harmful or even lethal. Nowadays a special sensor in infusion pumps is used to detect air in the line.

In traditional thermal flow sensors a small amount of heat is generated by a heat source and the liquid flow rate is deduced from a temperature sensor measuring the cooling effect of the flowing liquid. The observed cooling down is the same for both flow directions (forwards and backwards), leading to a lack of sensitivity at low flow rates in the vicinity of a vanishing flow rate. This problem can be remedied by using a differential measuring procedure involving two temperature sensors, wherein one temperature sensor is arranged downstream the heat source and the other one is arranged upstream the heat source This measuring technique also has the advantage of receiving a faster signal response as well as a reduced dependency on the temperature of the liquid.

However, when such a differential signal is used, the presence of a gas or air bubble in the sensor cannot be distinguished in a satisfying manner from a no-flow condition where the line is filled with liquid, but the liquid stands still (zero flow rate).

SUMMARY

Based on the above, the problem underlying the present invention therefore is to provide a flow sensor as well as a corresponding method that is capable of determining the presence of a gas (e.g. air) bubble in the liquid to be processed by the flow sensor while guaranteeing at the same time an excellent sensitivity of the sensor in case of low flow rates of the fluid medium to be measured.

This problem is solved by a flow sensor having the features of claim 1.

Preferred embodiments of the present invention are stated in the corresponding sub claims and are described below.

BRIEF DESCRIPTION OF THE DRAWINGS

Further embodiments, features and advantages of the present invention will be described below with reference to the Figures, wherein.

DETAILED DESCRIPTION

Figure 1:
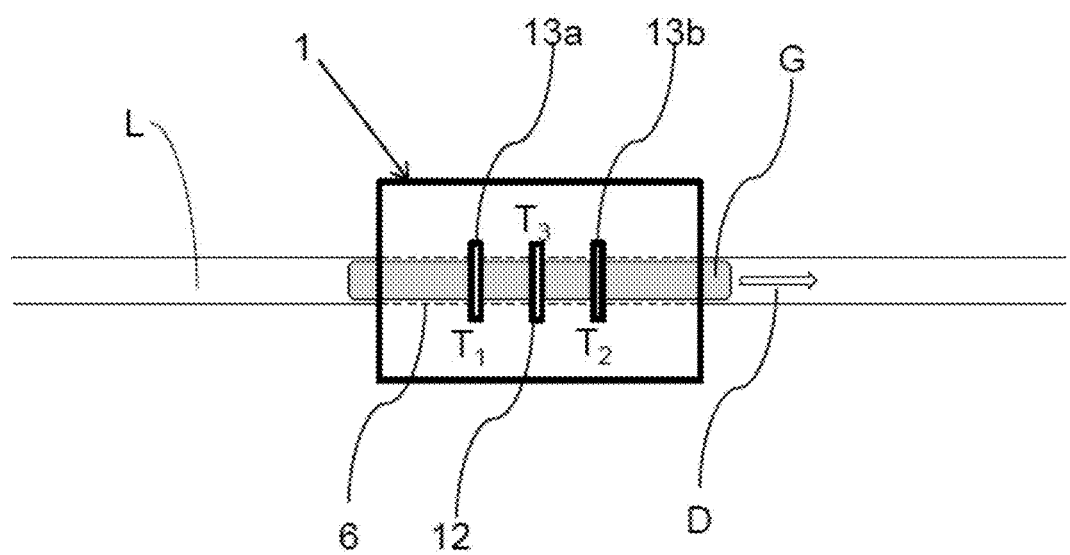
FIG. 1 shows a schematic illustration of a flow sensor according to the invention through which a gas (e.g. air) bubble flows which is detected by the flow sensor.

According to claim 1, the flow sensor comprises:
a first and a second temperature sensor,
a heat source,
a flow channel for guiding a liquid in a flow direction through the flow sensor,
wherein said heat source and said temperature sensors are configured such that they are in thermal contact with said liquid, when said liquid passes through said flow channel, and
wherein with respect to the flow direction the first temperature sensor is arranged upstream the heat source whereas the second temperature sensor is arranged downstream said heat source,
wherein, according to the invention, the flow sensor is configured to determine a temperature being proportional to the temperature of the heat source and further comprises an analyzing circuit which is configured to determine whether a gas bubble passes the flow channel using (as an input) at least said temperature being proportional to the temperature of the heat source measured upon passing of said gas bubble through the flow channel.

It is to be noted, that within the framework of the present invention one is in principle able to distinguish between gas (e.g. air) and liquid (e.g. water or an aqueous solution) using only said temperature being proportional to the temperature of the heat source (i.e. the sum $T_3=T_1+T_2$ of the two temperatures $T_1$, $T_2$ measured by the first and second temperature sensor) since the heat dissipation in water/liquid is much higher than in air/gas.

According to an embodiment of the present invention, said temperature $T_3$ is the sum of said individual temperatures $T_1$ and $T_2$. One may also use an estimate of the actual temperature of the heat source, which is the average of the two temperatures $T_1$ and $T_2$ (i.e. $(T_1+T_2)/2$). However, one may also omit the factor ½ and take it into account when selecting the upper threshold described further below. Thus it is not necessary to use the actual temperature of the heat source; it suffices to use a value proportional to the actual temperature. Alternatively, instead of using said sum for determining the temperature $T_3$, one may also measure the temperature $T_3$ of the heat source directly. For instance be means of a dedicated separate temperature sensor or for instance, if the heat source is a resistive heater, by inferring the temperature from the temperature dependence of the electrical resistance of said heater. Here, the heat source itself would form the separate temperature sensor associated to the heat source.

According to an embodiment of the sensor according to the invention, the analyzing circuit is configured to conclude that a gas bubble has been detected in the flow channel and/or to generate a corresponding output signal indicating that a gas bubble has been detected in the flow channel, in case said temperature $T_3$ being proportional to the temperature of the heat source exceeds a pre-determined upper threshold $T_{lim}$.

Said upper threshold depends on the respective embodiment of the flow sensor and may be chosen by filling the flow channel with gas and measuring the corresponding sum of the temperatures $T_1$ and $T_2$, and further by filling the flow channel with a liquid and measuring the corresponding sum of the temperatures $T_1$ and $T_2$, wherein said upper threshold may be chosen to lie within the interval limited by said two sum signals and may lie in the middle of this interval.

Further, according to an embodiment of the present invention, the flow sensor or its analyzing circuit is configured to determine the temperature difference $$\Delta T = T_2 - T_1,$$

between a temperature $T_2$ measured by the second temperature sensor and a temperature $T_1$ measured at the same time by the first temperature sensor.

Further, preferably, the flow sensor or analyzing circuit is configured to determine the temperature of the heat source by determining the sum of the two temperatures $T_3 = T_2 + T_1$ (or alternatively, the flow sensor is configured to measure said temperature of the heat source by means of a (third) separate temperature sensor, wherein this temperature sensor may also be formed by the heat source itself (see above)).

In case $|\Delta T_1| < \Delta T_{lim}$ (where $\Delta T_{lim}$ is a constant lower threshold depending on the respective design/embodiment of the flow sensor) and $T_3 > T_{lim}$ is true, the analysing circuit is configured to conclude that a gas (e.g. air) bubble is present in the flow channel and/or to generate an output signal indicating that a gas (e.g. air) bubble is present in the flow channel. Preferably, the absolute value of $\Delta T$ is considered so that the flow direction D does not matter.

Further, in case $|\Delta T| < \Delta T_{lim}$ and $T_3 > T_{lim}$ is false, the analysing circuit is configured to conclude that the liquid in the flow channel stands still (e.g. there is an occlusion in, upstream, or downstream the flow channel of the flow sensor) and/or to generate an output signal indicating that the liquid in the flow channel stands still.

In the above, $\Delta T_{lim}$ is close to zero and may be chosen to correspond to the resolution of the sensor at low flow rates.

In other words, the difference in reading between the second temperature sensor downstream and a first temperature sensor upstream of the heat source gives almost zero if the liquid is standing still or air fills the flow sensor. By measuring also the temperature of the heater (or a temperature proportional thereto, e.g. the sum of these two temperature sensor readings) the medium inside the flow sensor can be determined, and gas (particularly air) can be distinguished from standing liquid (particularly water and aqueous solutions) because of its significant difference in thermal conductivity and heat capacity. Namely, when air is present in the flow channel heat from the heat source is dissipated less and the temperature $T_3$ gets hotter compared to the case when liquid fills the flow channel.

According to a preferred embodiment of the present invention, the flow sensor (particularly the analyzing circuit) is configured to determine the temperature of the heat source being proportional to the temperature of the heat source as (or using) the sum of the temperatures measured by the first and the second temperature sensor.

Preferably, the flow sensor is configured to generate a (e.g. binary) signal and to output said signal, which signal indicates whether a gas (e.g. air) bubble is currently passing the flow channel or not.

Further, according to a preferred embodiment of the present invention, the analyzing means is also configured to determine one of: the flow velocity, the mass flow rate, and/or the volumetric flow rate of said liquid using the temperatures measured by the first and second temperature sensor.

Further, according to a preferred embodiment of the present invention, the flow sensor comprises a semiconductor module that comprise a first side facing away from the flow channel and a second side facing the flow channel and/or adjacent the flow channel, wherein the semiconductor module preferably comprises a recess on its first side, which recess comprises a bottom, preferably in the form of an (e.g. dielectric) membrane that forms a part of said second side of the semiconductor module.

Further, according to an embodiment of the present invention, said heat source and said first and second temperature sensor are at least partially arranged on said bottom on the second side of the semiconductor module which may form a component side of the semiconductor module, so that the heat source and said temperature sensors are in thermal contact with the liquid in the flow channel. Here, particularly, the heat source and the temperature sensing means may contact the liquid via an intermediate layer of another material (e.g. a glass, a metal, a polymer, a liquid crystal polymer (LCP), preferably an aromatic polyester, preferably a fully aromatic polyester, preferably a copolymer comprising a 4-hydroxybenzoic acid residue and/or 6-hydroxynaphtene-2-carboxylic acid, preferably a 4-hydroxybenzoic acid/ 6-hydroxynaphtene-2-carboxylic acid copolymer (CAS Registry Number 70679-92-4)).

Preferably, also the analyzing circuit is arranged on the semiconductor module.

Preferably, according to an embodiment of the flow sensor according to the invention the flow sensor is a microscopic flow sensor (this preferably applies to all flow sensors described herein).

Further, preferably, the length of the flow sensors described herein in the flow direction is preferably smaller than 20 mm, preferably smaller than 15 mm, preferably smaller than 10 mm, preferably smaller than 5 mm, preferably smaller than 1 mm. Further, preferably, the inner diameter of the flow channel (e.g. across the flow direction) is preferably smaller than 20 mm, preferably smaller than 15 mm, preferably smaller than 10 mm, preferably smaller than 5 mm, preferably smaller than 1 mm.

Furthermore, the flow sensor is preferably configured to measure (as said liquid) an infusion liquid, particularly blood, an aqueous solution, a saline solution, a physiological saline solution, a drug in physiological saline or blood. Here, the gas bubbles to be detected are particularly air bubbles.

Furthermore, according to another aspect of the present invention, a method for determining the presence of a gas bubble in a liquid flowing through a flow sensor is disclosed, wherein the method preferably uses a flow sensor according to the invention as described herein, and further comprises the steps of:

letting a liquid pass through a flow channel so that the liquid successively passes a first temperature sensor, a heat source and a second temperature sensor, which sensors and heat source are in thermal contact with the liquid, determining a temperature $T_3$ being proportional to the temperature of the heat source upon passing of said liquid through the flow channel, and optionally measuring the temperature of the liquid at the first temperature sensor and at the second temperature sensor, and automatically detecting a gas bubble in the liquid using (as an input) at least said temperature being proportional to the temperature of the heat source and optionally also the temperature difference between said temperature at the second temperature sensor and said temperature at the first temperature sensor.

According to a preferred embodiment of the method according to the invention, said temperature $T_3$ being proportional to the temperature of the heat source is determined as or using the sum of the temperatures $T_1$, $T_2$ measured by the first and the second temperature sensor.

Further, according to an alternative preferred embodiment of the method according to the invention, said temperature $T_3$ is measured using a separate temperature sensor associated to the heat source (see also above).

Further, according to a preferred embodiment of the method according to the invention, it is automatically concluded that a gas bubble has been detected in the flow channel in case said temperature $T_3$ exceeds a pre-determined upper threshold $T_{lim}$ (see also above).

Further, according to a preferred embodiment of the method according to the invention, the temperature difference $\Delta T$ between said temperature $T_2$ at the second temperature sensor and said temperature $T_1$ at the first temperature sensor is automatically determined, wherein when said temperature difference $\Delta T$ is below a pre-defined lower threshold $\Delta T_{lim}$ (see also above) and said temperature $T_3$ being proportional to the temperature of the heat source exceeds a pre-determined upper threshold $T_{lim}$ (see also above) it is automatically concluded that a gas bubble has been detected in the flow channel, while in case said temperature difference $\Delta T$ is below said pre-defined lower threshold $\Delta T_{lim}$ and said temperature $T_3$ is below said pre-determined upper threshold $T_{lim}$ it is automatically concluded that the liquid in the flow channel stands still.

Preferably, according to an embodiment of the method according to the invention, an (e.g. binary) signal is generated and output, which signal indicates whether a gas (e.g. air) bubble is currently being detected in the flow channel or not.

Preferably, according to an embodiment of the method according to the invention, said liquid running through the flow sensor/flow channel is an infusion liquid (see above). Here, the gas bubbles to be detected are particularly air bubbles.

FIG. 1 shows a schematical representation of a flow sensor 1 according to the invention through which a liquid L, particularly a medical infusion liquid, is guided, which liquid L may comprise one or several gas (e.g. air) bubbles G. Particularly, in medical applications such as catheters, used in body lumens of human or animal patients it is important to detect such gas bubbles in order to protect the patient from harm.

Figure 2:
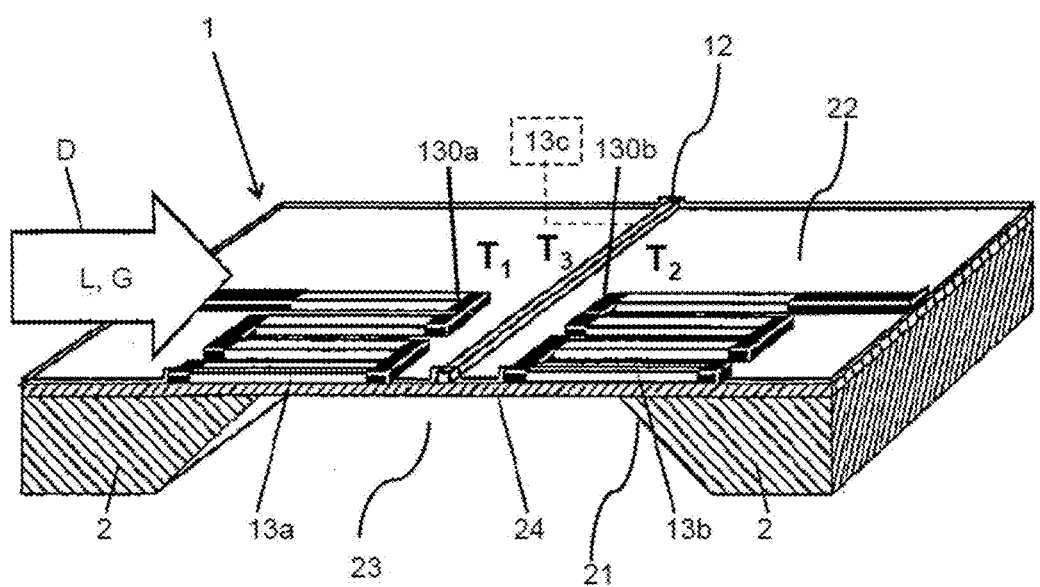
FIG. 2 shows a cross sectional view of an embodiment of a flow sensor according to the present invention.
Figure 3:
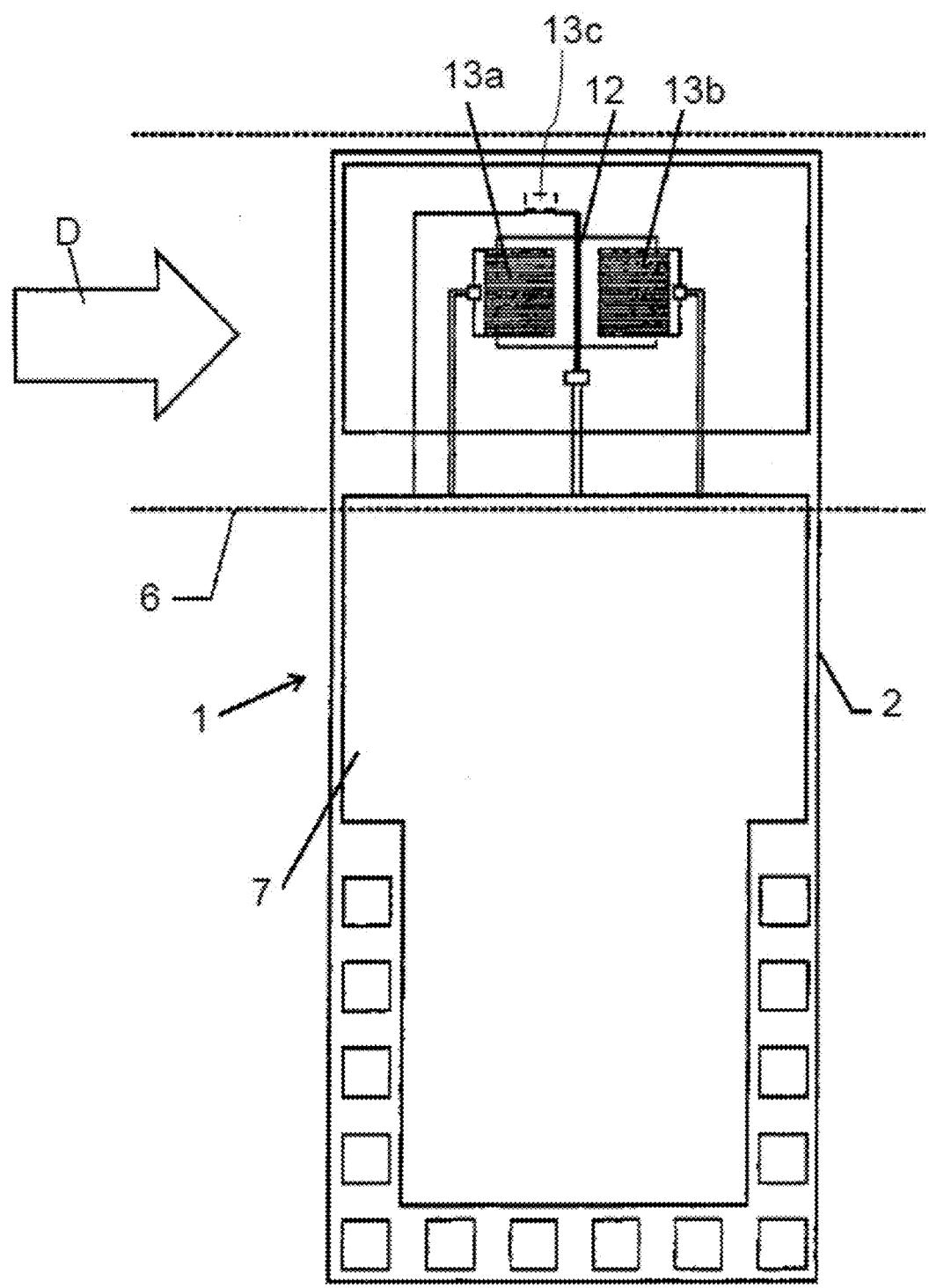
FIG. 3 shows a top view onto the flow sensor shown in FIG. 2.

Such a detection of gas bubbles G is implemented into the flow sensor 1 according to the invention which is further shown in an exemplary fashion in FIGS. 2 and 3.

The flow sensor 1 is adapted for measuring at least one of the flow velocity, the mass flow rate, and the volumetric flow rate of a liquid L or any fluid medium guided through the flow sensor 1. To this end, the flow sensor 1 may comprise a semiconductor module 2 on which a first and a second temperature sensor 13a, 13b and a heat source 12 are arranged, a flow channel 6 for guiding said liquid L in a flow direction D, wherein said heat source 12 and said temperature sensing means 13a, 13b are configured such that they are in thermal contact with the liquid L when the latter is passed through the flow channel 6.

As shown in FIG. 2, the semiconductor module 2 comprises a first side 21 facing away from the flow channel 6 and a second side 22 facing said channel 6. Further, the semiconductor module 2 comprises a recess 23 on said first side 21 which comprises a thin bottom 24 (e.g. in the form of a dielectric membrane) that forms a part of said second side 22 of the semiconductor module 2.

The heat source 12 and said temperature sensing means 13a, 13b are at least partially arranged on said bottom 24 on the second side 22 of the semiconductor module 2 (cf. FIG. 2) so that the heat source 12 and said temperature sensing means 13a, 13b are in thermal contact with the liquid L (or gas bubble G)

For measuring the flow velocity of the liquid L or related quantities (see above) the two temperature sensors 13a, 13b are arranged on opposite sides of the heat source 12, wherein with respect to said flow direction D, the first temperature sensor 13a is arranged upstream said heat source 12 and the second temperature sensor 13b is arranged downstream said heat source 12.

As indicated in FIGS. 2 and 3 the heat source 12 and the temperature sensors 13a, 13b may be formed by an integrated circuit that is arranged on the second (component) side 22 of the semiconductor module 2, particularly using a CMOS technique. Here, the heat source 12 may be formed by a resistor. The two temperature sensors 13a, 13b may be formed as thermopiles, respectively.

Particularly, the heat source 12 and at least the inner contact rows 130a, 130b of the thermopiles 13a, 13b are arranged on the bottom 24 of the recess 23 on the second side 22 of the semiconductor module 2 and are in thermal contact with the liquid L passing along the bottom 24. A layer comprising one of the following materials: a glass, a metal, a plastic, an LCP (see also above) may be arranged between the liquid L and the temperature sensors 13a, 13b or heat source 12.

Furthermore, an analyzing circuit 7 is arranged on the semiconductor module 2, which circuit 7 is configured to operate the heat source 12, particularly with a constant current, a constant temperature, a constant voltage, pulsed, or modulated. Furthermore, the analyzing circuit 7 is configured to measure the temperatures $T_1$, $T_2$ at the inner contact rows 130a, 130 of the thermopiles 13a, 13b (the outer contact rows of the thermopiles 13a, 13b are essentially on the same temperature level) and to determine the difference $T_2-T_1$.

The heat source 12 is configured to generate a temperature distribution in said liquid L that flows along the first sensor 13a, the heat source 12 and the second sensor 13b, wherein due to the flow of the liquid L in the flow channel 6 in the flow direction D said temperature distribution becomes asymmetric which is reflected in said temperature difference $\Delta T = T_2 - T_1$ measured with help of the two temperature sensors 13a, 13b. Therefore, said temperature difference $\Delta T$ provides a measure for the flow velocity. The analyzing circuit 7 is configured to derive from this temperature difference a suitable measuring value, such as flow velocity, volumetric flow rate, or mass flow rate of the liquid.

In order to determine, whether a gas bubble G passes the sensor 1 (i.e. the flow channel 6), the analyzing circuit 7 uses the fact that said temperature difference $T_2-T_1$ is essentially zero when the flow velocity of the liquid L in the flow channel is zero or when a gas bubble G passes the flow channel 6 as indicated in FIG. 1. In case of the gas bubble G said temperature difference $T_2-T_1$ is zero due to the fact that the thermal conductivity of a gas (e.g. air) is far lower than that of a liquid (e.g. water etc.) so that the temperature distribution induced by the heater 12 stays essentially symmetric rendering said temperature difference $\Delta T$ essentially zero.

The analyzing means 7 is now configured to determine the thermal conductivity of the medium in the flow channel 6 when said temperature difference $\Delta T$ is essentially zero, namely below the threshold $\Delta T_{lim}$ described herein, by measuring the temperature of the heat source 12 or a temperature proportional to the temperature of the heat source 12. This temperature $T_3$ can be determined by measuring the heat source temperature directly using an optional temperature sensor 13c, by averaging over the temperatures $T_1$ and $T_2$, or by simply considering the sum of these two temperatures $T_1$ and $T_2$ (see also above), i.e. using the first and the second temperature sensor 13a, 13b.

In case the thermal conductivity of the medium inside the flow channel 6 is below a certain threshold (e.g. the temperature T3 is above said pre-determined threshold $T_{lim}$ described herein), the analyzing circuit 7 concludes that the medium in the flow channel 6 is a gas bubble. This is possible due to the fact that the thermal conductivity and heat capacity of a gas (e.g. air) is typically significantly lower than the thermal conductivity of a liquid (e.g. $H_2O$: 0.6 W/m*K; air: ~0.025 W/m*K).

We claim:

1. A flow sensor for detecting a gas bubble in a liquid flowing through the flow sensor, wherein the flow sensor comprises:
    a first and a second temperature sensor configured to measure temperature,
    a heat source,
    a flow channel for guiding a liquid in a flow direction,
    wherein said heat source and said temperature sensors are configured such that they are in thermal contact with said liquid, when said liquid passes through said flow channel, and
    wherein with respect to the flow direction the first temperature sensor is arranged upstream the heat source whereas the second temperature sensor is arranged downstream the heat source,
wherein the flow sensor is configured to determine a temperature of the heat source and further comprises an analyzing circuit which is configured to detect a gas bubble in the flow channel using at least said temperature of the heat source; and,
wherein the flow sensor or the analysing circuit is configured to determine said temperature of the heat source using the sum of the temperatures measured by the first and the second temperature sensor.

2. The flow sensor according to claim 1, wherein the flow sensor comprises a further temperature sensor that is configured to measure said temperature of the heat source.

3. The flow sensor according to claim 1, wherein the analyzing circuit is configured to conclude that a gas bubble has been detected in the flow channel in case said temperature of the heat source exceeds a pre-determined upper threshold.

4. The flow sensor according to claim 1, wherein the flow sensor or the analyzing circuit is configured to determine a temperature difference between said temperature at the second temperature sensor and said temperature at the first temperature sensor, wherein the analyzing circuit is configured to conclude that a gas bubble has been detected in the flow channel when said temperature difference is below a pre-defined lower threshold and said temperature of the heat source exceeds a pre-determined upper threshold, and wherein the analyzing circuit is configured to conclude that the liquid in the flow channel stands still, when said temperature difference is below said pre-defined lower threshold and said temperature of the heat source is below said pre-determined upper threshold.

5. The flow sensor according to claim 1, wherein the analyzing circuit is configured to determine one of: the flow velocity, the mass flow rate, and/or the volumetric flow rate of said liquid using the temperatures measured by the first and second temperature sensor.

6. The flow sensor according to claim 1, wherein the flow sensor comprises a semiconductor module that comprise a first side facing away from the flow channel and a second side facing the flow channel, wherein the semiconductor module comprises a recess in its first side, which recess comprises a bottom that forms a part of said second side of the semiconductor module.

7. The flow sensor of claim 6, wherein said heat source and said first and second temperature sensor are at least partially arranged on said bottom on the second side of the semiconductor module.

8. The flow sensor according to claim 1, wherein said liquid is an infusion liquid.

9. A flow sensor for detecting a gas bubble in a liquid flowing through the flow sensor, wherein the flow sensor comprises:
    a first and a second temperature sensor configured to measure temperature,
    a heat source,
    a flow channel for guiding a liquid in a flow direction,
    wherein said heat source and said temperature sensors are configured such that they are in thermal contact with said liquid, when said liquid passes through said flow channel, and
    wherein with respect to the flow direction the first temperature sensor is arranged upstream the heat source whereas the second temperature sensor is arranged downstream the heat source,
wherein the flow sensor is configured to determine a temperature of the heat source and further comprises an analyzing circuit which is configured to detect a gas bubble in the flow channel using at least said temperature of the heat source, wherein the flow sensor or the analysing circuit is configured to determine said temperature of the heat source using the sum of the temperatures measured by the first and the second temperature sensor.

10. A flow sensor for detecting a gas bubble in a liquid flowing through the flow sensor, wherein the flow sensor comprises:
    a first and a second temperature sensor configured to measure temperature,
    a heat source,
    a flow channel for guiding a liquid in a flow direction,
    wherein said heat source and said temperature sensors are configured such that they are in thermal contact with said liquid, when said liquid passes through said flow channel, and
    wherein with respect to the flow direction the first temperature sensor is arranged upstream the heat source whereas the second temperature sensor is arranged downstream the heat source, wherein the flow sensor is configured to determine a temperature of the heat source and further comprises an analyzing circuit which is configured to detect a gas bubble in the flow channel using at least said temperature of the heat source, and wherein the flow sensor or the analyzing circuit is configured to determine a temperature difference between said temperature at the second temperature sensor and said temperature at the first temperature sensor, wherein the analyzing circuit is configured to conclude that a gas bubble has been detected in the flow channel when said temperature difference is below a pre-defined lower threshold and said temperature of the heat source exceeds a pre-determined upper threshold, and wherein the analyzing circuit is configured to conclude that the liquid in the flow channel stands still, when said temperature difference is below said pre-defined lower threshold and said temperature of the heat source is below said pre-determined upper threshold.

11. A method for detecting a gas bubble in a liquid flowing through a flow sensor, wherein the method comprises the steps of:

letting a liquid pass through a flow channel so that the liquid successively passes along a first temperature sensor, a heat source and a second temperature sensor, determining a temperature of the heat source upon passing of said liquid through the flow channel, wherein preferably also the temperature of the liquid at the first temperature sensor and at the second temperature sensor are measured upon passing of said liquid through the flow channel, and detecting a gas bubble comprised by the liquid in the flow channel using at least said temperature being proportional to the temperature of the heat source;

wherein said temperature of the heat source is determined using the sum of the temperatures measured by the first and the second temperature sensor.

12. The method according to claim 11, characterized in that said temperature of the heat source is measured using a separate temperature sensor associated to the heat source.

13. The method according to claim 11, characterized in that it is automatically concluded that a gas bubble has been detected in the flow channel in case said temperature of the heat source exceeds a pre-determined upper threshold.

14. The method according to claim 11, characterized in that the temperature difference between said temperature at the second temperature sensor and said temperature at the first temperature sensor is determined, wherein when said temperature difference is below a pre-defined lower threshold and said temperature of the heat source exceeds a pre-determined upper threshold it is automatically concluded that a gas bubble has been detected in the flow channel, while in case said temperature difference is below said pre-defined lower threshold and said temperature of the heat source is below said pre-determined upper threshold it is automatically concluded that the liquid in the flow channel stands still.

15. The method according to claim 11, wherein said liquid is an infusion liquid.

* * * * *